United States Patent [19]
Gluck et al.

[11] Patent Number: 4,976,261
[45] Date of Patent: Dec. 11, 1990

[54] ENDOTRACHEAL TUBE WITH INFLATABLE CUFFS

[75] Inventors: Eric H. Gluck, West Hartford; Brian E. Thompson, Colchester; Michael A. Hall, Glastonbury, all of Conn.

[73] Assignee: Advanced Pulmonary Technologies, Inc., Glastonbury, Conn.

[21] Appl. No.: 331,815

[22] Filed: Apr. 3, 1989

[51] Int. Cl.⁵ ............................................. A61M 16/00
[52] U.S. Cl. ............................... 128/207.15; 604/102; 604/103
[58] Field of Search ....................... 128/207.15, 207.14, 128/207.16, 207.17, 344, 101

[56] References Cited

U.S. PATENT DOCUMENTS

| | | | |
|---|---|---|---|
| 2,175,726 | 10/1939 | Gebauer | 604/102 |
| 2,210,744 | 10/1940 | Winder . | |
| 2,854,982 | 11/1958 | Pagano . | |
| 2,930,377 | 3/1960 | Cowley | 604/103 |
| 3,034,510 | 4/1962 | Kittel . | |
| 3,173,418 | 3/1965 | Baran | 128/207.15 |
| 3,731,692 | 7/1973 | Goodyear . | |
| 3,890,976 | 11/1975 | Bazell et al. . | |
| 4,046,139 | 2/1977 | Horn . | |
| 4,090,518 | 5/1978 | Elam | 128/207.15 |
| 4,091,816 | 10/1978 | Elam . | |
| 4,231,365 | 1/1980 | Scarberry . | |
| 4,248,221 | 2/1981 | Winward | 128/207.15 |
| 4,327,720 | 5/1982 | Bronson et al. | 128/207.15 |
| 4,329,993 | 5/1982 | Lieber et al. . | |
| 4,335,723 | 7/1982 | Patel . | |
| 4,344,436 | 8/1982 | Kubota . | |
| 4,367,740 | 1/1983 | Evanoski | 604/102 |
| 4,383,534 | 5/1983 | Peters | 128/207.15 |
| 4,419,095 | 4/1983 | Nebergall et al. . | |
| 4,423,725 | 1/1984 | Baran et al. | 128/207.15 |
| 4,456,011 | 10/1984 | Warnecke . | |
| 4,573,966 | 11/1986 | Weikl et al. . | |
| 4,584,998 | 4/1986 | McGrail | 604/102 |
| 4,607,635 | 8/1986 | Heyden | 128/207.15 |
| 4,661,095 | 4/1987 | Taller et al. | 604/103 |
| 4,676,228 | 6/1987 | Krasner et al. . | |
| 4,688,568 | 8/1987 | Frass et al. | 128/207.15 |
| 4,690,138 | 9/1987 | Heyden | 128/207.15 |
| 4,700,700 | 10/1987 | Eliachar . | |
| 4,751,924 | 6/1988 | Hammerschmidt | 604/102 |
| 4,834,087 | 5/1989 | Coleman et al. | 128/207.15 |
| 4,850,348 | 7/1989 | Pell et al. | 604/100 |

*Primary Examiner*—Eugene H. Eickholt
*Attorney, Agent, or Firm*—Chilton, Alix & Van Kirk

[57] ABSTRACT

An endotracheal tube for artificial ventilation employs a primary cuff and a secondary cuff for locating and positioning the tube in the trachea of a patient. The secondary cuff employs a balloon sleeve which is located in close proximity to the distal end of the tube. The secondary balloon sleeve is sealed against the tube in a reverse folded configuration. The tube wall includes a number of lumens which may be employed for various auxiliary functions.

15 Claims, 2 Drawing Sheets

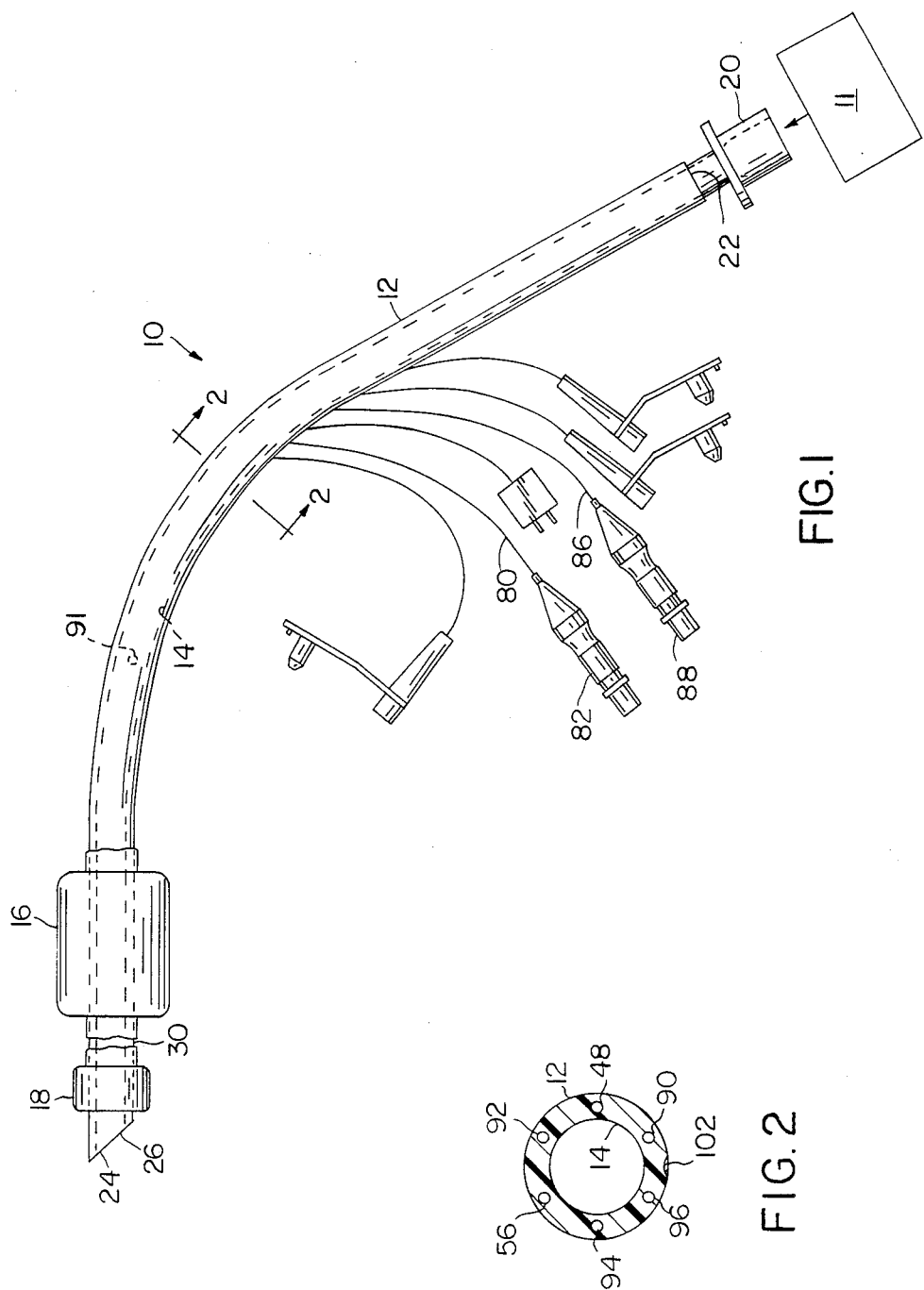

ENDOTRACHEAL TUBE WITH INFLATABLE CUFFS

BACKGROUND OF THE INVENTION

This invention relates generally to endotracheal tubes which are inserted through the mouths of patients to facilitate artificial ventilation. More particularly, the present invention relates to endotracheal tubes which employ inflatable structures to provide an air-tight seal between the tube and the surrounding tracheal wall.

Endotracheal tubes which are inserted through the mouth or nasal passages of a patient for extension into the trachea have been widely used in the medical arts for a number of years. Such endotracheal tubes conventionally employ an external inflatable sleeve or cuff. The tube is insertable into the trachea. The cuff is then inflated with air or other fluids to produce an air-tight seal between the tube and the surrounding body tissue. The cuff is conventionally located at various positions along the inner wall of the pharynx, larynx or trachea according to the specific endotracheal tube design. A wide variety of various forms of endotracheal tubes have been employed.

While conventional endotracheal tubes have been advantageously employed to provide numerous beneficial medical achievements, one of the most prominent problems associated with endotracheal tubes in general is the tissue damage which is caused due to contact between the endotracheal tube, and in particular, the distal end portions of the tube, and the very delicate tissues which line the trachea and the larynx. During periods of prolonged intubation, contact and pressure from the tube may have a pronounced effect on surrounding tissue, and in some instances, result in the formation of scar tissue. A number of devices have been proposed for reducing the contact between the endotracheal tube and the surrounding tissue during prolonged intubation. Devices such as shown Gebauer U.S. Pat. No. 2,175,726, Winder U.S. Pat. No. 2,210,744, Elam U.S. Pat. No. 4,091,816 and Eliachar U.S. Pat. No. 4,700,700 have employed plural cuff arrangements to minimize contact between the tube and the tissue.

Eliachar U.S. Pat. No. 4,700,700 discloses an endotracheal tube which employs an upper inflatable-deflatable cuff which is fixed in position above the larynx. The upper cuff surrounds a predetermined portion of the posterior round surface of the tube. A lower inflatable-deflatable cuff, which is spaced from the upper cuff, is positioned at a pre-determined distance below the larynx. The upper cuff is operative when inflated to engage a posterior portion of the pharynx to effect an alignment of the tube relative to the larynx wherein the axis of the tube portion within the larynx is maintained central thereto away from the posterior portion of the larynx and the lower cuff is operative upon inflation to sealingly engage the inner wall of the trachea. The cuffs are separately inflatable and deflatable. Channels in the wall of the tube extend from the cuffs to an upper portion of the tube for inflating and deflating the cuffs.

Elam U.S. Pat. No. 4,091,816 discloses an endotracheal tube which employs two inflatable cuffs. The balloons are shaped and positioned to fully occupy the spaces above and below the open larynx. The two cuffs have a common inflation channel which freely communicates between the cuffs. Elastic properties of the upper cuff cooperate to form a pressure relief system for the lower cuff which is essentially non-elastic. A relatively short segment of uncuffed tube facilitates the obtaining of a pre-determined anatomical location of the cuffs and resultant selective positioning of the tube within the trachea. The seals of the cuffs can be maintained at a relatively low pressure.

Although the use of various double cuff arrangements have proved somewhat satisfactory, optimal use of endotracheal tubes can be enhanced with additional refinements to the spacial relationships and dimensional relationships between the cuffs or balloons, as well as additional refinements to the cuff design and the placement of the tube in the patient. Accordingly, the present invention is directed to providing an improved endotracheal tube having a double inflatable cuff arrangement.

SUMMARY OF THE INVENTION

Briefly stated, the invention in a preferred form, is an endotracheal tube which is adapted for insertion into the trachea. The tube includes an elongated tubular structure defining a central ventilation passage which extends between a proximal end and a distal end terminating at a tip. An inflatable primary fixation/sealant sleeve encircles the tube between the proximal and distal ends for sealing the tube against the tracheal wall upon inflation of the sleeve. A second inflatable locating sleeve encircles the tube at the distal end in close proximity to the tip for centering the tube at a lower portion of the trachea upon inflation. The axis of a linear distal end segment of the tube is thus constrained to be generally coaxial with the central axis of the trachea. A manually operable device, for selectively inflating and deflating the primary sleeve, communicates through a first lumen which is formed in the wall of the tube to convey the requisite pressurized fluid to the sleeve. Another manually operable device, for selectively inflating and deflating the second sleeve, communicates through a second lumen which extends longitudinally in the wall of the tube.

In one embodiment of the invention, the inflated diameter of the primary fixation sleeve compared to the inflated diameter of the secondary locating sleeve is on the order of three to two. The secondary locating sleeve is located as close as possible to the tube tips and in one reduction to practice is three millimeters from the distal tip of the tube. The locating sleeve is formed by sealing a reverse folded portion of an inflatable balloon sleeve against the exterior tube surface. The tube wall may also have a plurality of additional lumens for monitoring various functions and introducing various substances into the central respiratory channel.

An object of the invention is to provide a new and improved endotracheal tube.

Another object of the invention is to provide a new and improved endotracheal tube having improved means for inhibiting contact between the tube and the surrounding tracheal tissue and possible tracheal abrasion during intubation.

A further object of the invention is to provide a new and improved endotracheal tube which may be used during periods of prolonged intubation and at high ventilation rates while reducing adverse effects due to contact and pressure between the tube and the surrounding body tissue.

Other objects and advantages of the invention will become apparent from the drawings and the specification.

BRIEF DESCRIPTION OF THE DRAWINGS

FIG. 1 is a side view, partly broken away and partly in schematic, of an endotracheal tube in accordance with the present invention;

FIG. 2 is a an enlarged cross-sectional view of the endotracheal tube of FIG. 1 taken along the line 2—2 thereof.

DETAILED DESCRIPTION OF THE INVENTION

Figure 4:
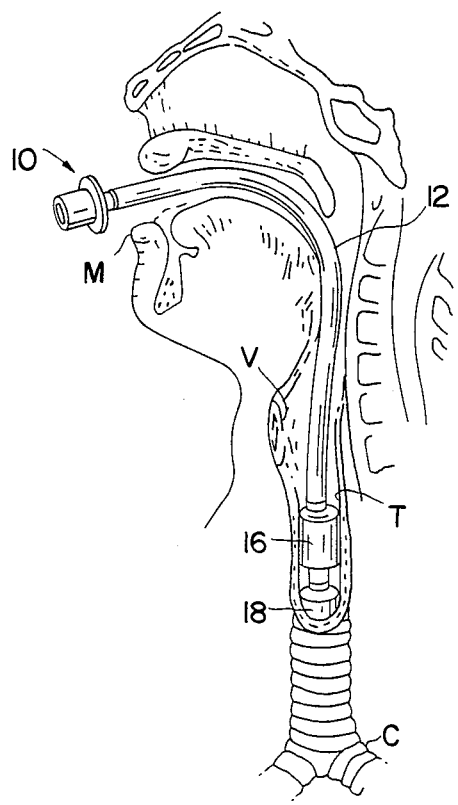
FIG. 4 is a fragmentary side view of the endotracheal tube of FIG. 1 further illustrating the tube in a mounted position within a patient.

With reference to the drawings, wherein like numerals represent like parts throughout the figures, an endotracheal tube in accordance with the present invention is generally designated by the numeral 10. Endotracheal tube 10 is adapted for insertion through the mouth M into the trachea T to facilitate artificial ventilation as best illustrated in FIG. 4. The tube 10 may be coupled to a ventilator 11 which is preferably a jet ventilator as disclosed in U.S. Pat. No. 4,747,403. In addition, the endotracheal tube is adapted for providing a number of auxiliary functions including introduction of medication, temperature sensing, gas sampling and pressure sensing.

The endotracheal tube 10 comprises a flexible ventilation tube 12 which extends from a tube connector 20 at a proximal end 22 to a distal end 24. The tube forms a primary ventilation passage 14 of substantially uniform diameter. The distal end 24 terminates in a tapered tip. The ventilation passage 14 opens through a ventilation port 26 at the distal end. The tube 12 is formed of a flexible rigid plastic material such as medical grade polyvinyl chloride which resists collapse under high temperature and humidity conditions. The ventilation tube includes a linear segment 30 extending from the distal end portion thereof. The tube 12 is dimensioned to permit insertion through the mouth M and into the trachea T of a patient. In one embodiment, the passage 14 diameter is on the order of 8mm and the ventilation tube has a diameter on the order of 12mm. The linear segment 30 in a preferred embodiment extends approximately 100mm.

The endotracheal tube functions in a very efficient manner to inhibit tube contact with the laryngeal and tracheal tissue during intubation. This is principally achieved by the configuration and placement of a primary fixation/sealant cuff 16 and a secondary locating cuff 18. The endotracheal tube is specifically adapted so that, upon intubation, the primary cuff 16 is located in the trachea T below the vocal cords V, and the secondary cuff 18 is located in the lower trachea above the carina C, as illustrated in FIG. 4.

Figure 3:
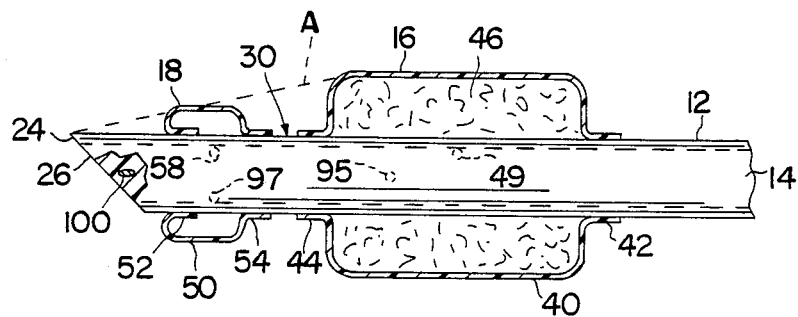
FIG. 3 is an enlarged fragmentary side sectional view of the endotracheal tube of FIG. 1.

With reference to FIG. 3, the primary fixation/sealant cuff 16 comprises an inclusive inflatable balloon sleeve 40. The balloon sleeve 40 has opposing spaced reduced end portions 42 and 44 which seal against the tube along cylindrical sleeve/pad interfaces to form a balloon sleeve which is inflatable and deflatable, as desired. In the deflated state (not illustrated), the balloon sleeve has a relatively smooth and uniform flattened surface to facilitate insertion into the patient. The surface of the sleeve 40 is preferably soft and slippery. The primary sleeve 40 is diametrically dimensioned so that upon inflation, the sleeve expands circumferentially to seal against the tracheal wall of the patient below the vocal cords V. Foam material 46 may be interposed in the sleeve interior to damp rocking movement.

A lumen 48 formed in the wall of the tube has a port 49 which opens into the interior of sleeve 40. The lumen 48 communicates at a proximal portion of the tube 12, via a connecting tube 80, with a syringe controlled valve 82 to provide a channel for pressurizing or depressurizing the balloon sleeve 40 as desired. The primary sleeve 40 expands to a relatively fixed limiting shape even though the inflation pressure exceeds the pre-established maximum inflation pressure threshold. The limiting shape is imposed in order to prevent pressure induced damage to the trachea T.

The locating cuff 18 is not inclusive and functions solely to center the distal end portion of the tube to inhibit tube contact with the tracheal wall. The secondary locating cuff 18 comprises a secondary balloon sleeve 50 which may have the same material composition as sleeve 40. The balloon sleeve 50 is located very close to the distal tip of the tube. In one preferred embodiment, the distal end of the sleeve 50 is three millimeters from the distal tip of tube 12. The balloon sleeve 50 includes a reduced end portion 52 which is sealed against the tube along a generally cylindrical sleeve/pad interface. The sleeve 50 is then reverse folded toward the proximal end to facilitate the close distal tip positioning of the inflatable balloon sleeve 50. The opposing reduced end 54 of the sleeve 50 is sealed against the tube along a generally cylindrical sleeve/pad interface. Since the distal end 52 of the sleeve 50 is reverse folded, the spaced sealing interfaces of the sleeve involve opposite sides of the sleeve In the deflated state (not illustrated), the balloon sleeve has a relatively smooth and flattened surface to facilitate insertion and removal of the tube.

The inflated diameter of the locating sleeve 50 in relation to the inflated diameter of the balloon sleeve 40 in the disclosed embodiment is approximately two to three in order to achieve the correct positioning and sealing of the endotracheal tube 10. For proper operation it is important that the centering balloon 50, when inflated, project beyond a line A which extends between the tip of the tube and the outside of inflated balloon 40 (FIG. 3). Also, balloon 50 is sized and shaped such that it cannot block the end of the tube when in the deflated condition (including subsequent to rupture). It should be appreciated that the locating cuff functions to center the lower end of the tube at the lower distal end portion thereof to thereby prevent contact of the tube tip with the trachea. By positioning the locating cuff 18 at a very close position in relation to the distal end 24, a very advantageous tube orientation is achieved whereby the axis of linear distal end segment 30 is generally parallel to the axis of the trachea.

The dimensions and relative location of cuffs 16 and 18 is important to achieving the most efficient and advantageous positioning of the endotracheal tube 10. In one embodiment, the effective inflatable lengths of sleeves 40 and 50 was approximately 40mm and 12mm, respectively, and the maximum inflated diameters was approximately 30mm and 20mm, respectively. The longitudinal spacing between the inflated sleeves was approximately 14mm to provide optimum location and sealing in the trachea. The balloon 50 will vary in size as the diameter of the tube varies.

A lumen 56 extends longitudinally in the wall of the tube 12 to a port 58 for communication with the interior of the secondary balloon sleeve 50. The lumen 56 communicates via tubing 86 with a syringe-controlled stop valve 88 for selectively inflating or deflating the balloon sleeve.

The tube 12 may optionally include additional angularly spaced lumens 90, 92, 94 and 96 which longitudinally extend in the tube wall to provide auxiliary monitoring and medicinal functions as best illustrated in FIG. 2. The lumens typically have a uniform diameter on the order of 1mm. Lumen 90 may function as a medication conduit and include a port 91 which opens into the central ventilation passage 14. Lumen 92 may provide a channel for receiving leads connecting an encapsulated temperature probe 100 positioned near the distal end of the tube. Lumen 94 may provide a channel for gas sampling. A sampling port 95 opens interiorly into passage 14 at the longitudinal position of the cuff 16. Lumen 96 may provide a channel for the measurement of the ventilation passage 14 pressure via port 97. Corresponding exterior tubing (schematically illustrated in FIG. 1) may communicate with appropriate syringes or pressure relief valves. A radio opaque strip 102 may also be included in tube 12 for longitudinal extension along the length of the tube for precisely determining the position of the tube by means of x-rays.

It should be appreciated that the endotracheal tube 10 as described provides a very efficient means for locating the tube within the trachea in a fashion which minimizes, if not eliminates, any contact of the tube with the sensitive laryngeal and tracheal tissue The primary fixation/sealant cuff 16 and the secondary locating 18 cuff are both deflated to a relative smooth, low profile configuration during initial introduction of the tube into the trachea. The primary sleeve 40 is inflated to seal the tube with the trachea T below the vocal cords V to prevent upper airway obstruction and to prevent upper airway secretions from entering into the lower tracheal regions. The locating sleeve 50 is then inflated to essentially center the distal end of the tube in the lower trachea. Sleeve 50 does not seal the lower trachea as such, but generally functions to provide a structure for achieving a proper tube orientation. Preferably, the distal end 24 is positioned approximately 3cm above the carina C. The close disposition of the locating cuff 18 to the distal end of the tube prevents the distal end from engaging the sensitive tracheal tissue. The central axis of the ventilation tube 12 and the trachea T are approximately coincident upon mounting and proper inflation of the sleeves 40 and 50. The cuffs 16 and 18 also effectively generally uniformly distribute the mounting and sealing pressures exerted by the tube throughout the surrounding tissue regions. Consequently, the adverse effects resulting from the engagement and pressure of the tube against the tracheal and other sensitive tissues are greatly reduced in comparison to conventional endotracheal tubes.

While a preferred embodiment of the foregoing invention has been set forth for purposes of illustration, the foregoing description should not be deemed a limitation of the invention herein. Accordingly, various modifications, adaptations and alternatives may occur to one skilled in the art without departing from the spirit and the scope of the present invention.

What is claimed is:

1. An endotracheal tube adapted for insertion through the mouth of a patient and into the patient's trachea comprising:
    elongated tube means having a proximal end and a distal end portion which terminates in a tip, said tube means defining a central ventilation passage;
    first inflatable means encircling said tube means between said proximal end and tip for generally centrally locating and sealing the tube means in the trachea upon the inflating thereof;
    non-occlusive second inflatable means spaced from said first inflatable means and encircling said tube means at said distal end portion in close proximity to said tip for preventing contact between said tube means tip and the trachea upon the inflating of said second inflatable means, said second inflatable means having an inflated diameter which is less than the inflated diameter of said first inflatable means;
    first inflating means for selectively inflating and deflating said first inflatable means; and
    second inflating means for selectively inflating and deflating said second inflatable means whereby upon the positioning of said tube means in the trachea of a patient and inflating of said first and second inflatable means the central axis of the patient's trachea is generally approximately coaxial with the axis of said tube means at said distal end portion.

2. The endotracheal tube of claim 1 wherein said second inflatable means is spaced approximately three millimeters from said distal end portion tip.

3. The endotracheal tube of claim 1 wherein upon inflation the ratio of the diameter of said second inflatable means to the diameter of said first inflatable means is on the order of two to three.

4. The endotracheal tube of claim 1 wherein said second inflatable means comprises a balloon sleeve having opposed first and second side surfaces and two spaced ends, said sleeve being sealed against said tube means on the first side surface and reverse folded and sealed at said second end against said tube means on the second side surface.

5. The endotracheal tube of claim 1 further comprising means defining a plurality of channels extending longitudinally through said tube means, one said channel communicating with said first inflatable means and a second said channel communicating with said second inflatable means.

6. The endotracheal tube of claim 1 further comprising a marking material mounted to said tube means and extending longitudinally thereof, said material being opaque to x-rays.

7. The endotracheal tube of claim 1 further comprising temperature sensing means disposed at a distal end portion of said tube means.

8. The endotracheal tube of claim 1 further comprising means defining a plurality channels extending longitudinally of said tube means in angularly spaced relationship and communicating through respective ports into said ventilation passage.

9. The endotracheal tube of claim 1 wherein the inflated diameter of said first inflatable means is greater than that of said second inflatable means and wherein said second inflatable means when inflated projects radially outwardly relative to the axis of said tube means to a point beyond a straight line extending between said tube means tip and the exterior of said inflated first inflatable means.

10. An endotracheal tube adapted for insertion through the mouth of a patient and into the patient's trachea comprising:

elongated tube means having a proximal end and a distal end portion which terminates in a tip, said tube means defining a central ventilation passage and a plurality of longitudinally extending conduits;

primary inflatable means comprising a primary sleeve interiorly communicating with one of said conduits and encircling said tube means between said proximal end and tip for generally centrally locating and sealing the tube means in the trachea upon inflation thereof; and non-occlusive secondary inflatable means spaced from said primary inflatable means, said secondary inflatable means comprising a secondary sleeve interiorly communicating with another of said conduits and encircling said tube means at said distal end portion in close proximity to said tip for generally centering said tube means in the trachea upon inflation thereof, said secondary sleeve having an inflated diameter which is less than the inflated diameter of said primary sleeve, said secondary sleeve also having two spaced end portions and two opposed side surfaces, one of said secondary sleeve end portions being sealed against said tube means on the first of said side surfaces thereof and the second said end portion of said secondary sleeve being sealed against said tube means on the second side surface thereof, said one end portion of said secondary sleeve being located in close proximity to said tip of said distal end portion of said tube means whereby upon positioning said tube means in the trachea of a patient and the inflating of said primary and secondary inflatable means sleeves the central axis of the trachea will be generally approximately coaxial with the axis of said tube means at said distal end portion thereof.

11. The endotracheal tube of claim 10 wherein said secondary sleeve one end portion is spaced approximately three millimeters from said distal tip.

12. The endotracheal tube of claim 10 wherein upon inflation the ratio of the diameter of said secondary inflatable means to the diameter of said primary inflatable means is on the order of two to three.

13. The endotracheal tube of claim 10 wherein said secondary sleeve end portions seal against said tube means along substantially cylindrical interfaces.

14. The endotracheal tube of claim 10 wherein said primary inflatable means is positionable for sealing below the vocal cords and the distal tip is positionable in the trachea approximately three centimeters above the carina.

15. The endotracheal tube of claim 10 wherein each of said inflatable means comprises a balloon generally coaxial with said tube means, said balloons have spaced reduced end portions of generally cylindrical shape commensurate with the surface portions of said tube means.

* * * * *